United States Patent [19]

Kyle et al.

[11] Patent Number: 5,795,783
[45] Date of Patent: Aug. 18, 1998

[54] CONTROL SOLUTIONS AND A METHOD OF USE THEREFOR

[75] Inventors: Jimmie R. Kyle, Simi Valley; Leonard Spolter, Granada Hills; Marcus Villagran, La Habra, all of Calif.

[73] Assignee: International Remote Imaging Systems, Inc., Chatsworth, Calif.

[21] Appl. No.: 618,101

[22] Filed: Mar. 19, 1996

[51] Int. Cl.$^6$ ........................................ G01N 31/00
[52] U.S. Cl. ..................... 436/8; 436/164; 436/169; 422/55; 422/56
[58] Field of Search ................... 436/8–16, 19, 436/164, 169; 422/55–56

[56] References Cited

U.S. PATENT DOCUMENTS

| | | | |
|---|---|---|---|
| 4,473,530 | 9/1984 | Villa-Real | 422/58 |
| 4,643,976 | 2/1987 | Hoskins | 436/8 X |
| 4,683,209 | 7/1987 | Ismail et al. | 436/8 X |
| 5,071,623 | 12/1991 | Akutsu | 422/56 |
| 5,516,700 | 5/1996 | Smith et al. | 436/164 |

*Primary Examiner*—Maureen M. Wallenhorst
*Attorney, Agent, or Firm*—Limbach & Limbach L.L.P.

[57] ABSTRACT

An analyte control solution system tests a plurality of identical test strips, with each test strip having a plurality of different reactive chemicals attached on pads. The analyte control solution system has a first mixture of a first plurality of different analytes, with each of the first plurality of different analytes not reacting with one another, but reacting with a different one of the dipstick pads to generate a visual indicator. The first plurality of different analytes do not react with all of the pads attached to each test strip. Another control solution has a second mixture, physically different from the first mixture, of a second plurality of different analytes. Each of the second plurality of different analytes does not react with one another, but reacts with a different one of the plurality of different reactive chemicals on the test strip to generate a visual indicator. The second plurality of different analytes do not react with any of the different reactive chemicals (on the dipstick pads) reacting to the analytes of the first mixture.

7 Claims, 1 Drawing Sheet

5,795,783

CONTROL SOLUTIONS AND A METHOD OF USE THEREFOR

FIELD OF THE INVENTION

The present invention relates to stable control solutions for testing reagents, such as the reagents on medical dipsticks, and more particularly to a control solution comprising a plurality of analytes in which interaction between the various analytes is minimized.

BACKGROUND OF THE INVENTION

A medical dipstick is an elongated strip with a plurality of pads formed or attached thereto. Each pad contains a reactive chemical or reagent that reacts with certain substances to generate a visual signal. Providing each pad with a different reactive reagent enables the use of the medical dipstick for determination of the status of a fluid to be tested. For example, the user would dip the medical dipstick into a sample to be tested, such as urine, and then observe which pads visually react with the sample. The combination of pad reactions indicate the status of the sample.

The visual reactions can be a simple color change whereby a color change indicates the presence of a particular substance in the sample. More sophisticated tests could involve different shades of color changes. Each pad would be testing something different. For example, a reagent A on pad 1 would test for the presence of glucose, a reagent B on pad 2 would test for the presence of nitrite, and so on. By knowing which pads test for what substance, the combination of color changes and locations of color changes from a single exposure of the medical dipstick to a sample would visually indicate the status of that sample.

A plurality of medical dipsticks are typically bundled together in a single container. The container prevents contamination and reduces the deterioration of the medical dipsticks stored therein. However, to ensure the accuracy of dipstick testing, the dipsticks in a particular container need to be tested periodically to ensure that the reagents on the pads have not been contaminated or degraded. The present method used for testing the performance of the medical dipsticks is to employ two test solutions. The first test solution tests for all positive results, while the second solution tests for absence of any analytes, all negative results. The first solution contains all of the substances that are being tested for. The second test solution is a saline solution which may contain various substances, but it contains none of the substances that are being tested for. To test the performance of medical dipsticks, prior to the analysis of a clinical specimen, two dipsticks are used. One is dipped into test solution one, and the other is dipped into test solution two. If the dipstick exposed to the first test solution shows a totally positive result, where all of the pads change to the appropriate color, and the second dipstick exposed to the second test solution shows a totally negative result, where none of the pads changes color, then the medical dipsticks are deemed to have not been degraded and may be used to perform the analysis of a clinical specimen.

The problem with the above test is that the test solution containing all of the substances being tested for can be unstable. The analytes in the test solution may react with one another, thus interfering with their proper reaction with the pads on the medical dipstick. For example, if bilirubin is present in test solution number one, it may be inactivated by interaction with other components in test solution number one.

SUMMARY OF THE INVENTION

The present invention solves the above-mentioned problem by providing a plurality of stable test solutions with the test solutions collectively testing all the pads. A first control solution contains a mixture of a first plurality of different active chemicals, with each of the first plurality of different active chemicals reacting chemically with a different reactive-chemical-containing pad, to generate a visual indicator. The first plurality of different active chemicals do not react chemically with all of the pads of each test strip. One or more additional control solutions contain a mixture of a second plurality of different active chemicals. Each of the second plurality of different active chemicals reacts chemically with a different one of the pads to generate a visual indicator. The second plurality of different active chemicals do not react chemically with any of the different reactive chemicals on the pads of each test strip reacting with the first plurality of different active chemicals. Collectively, the second plurality of different active chemicals reacts chemically with all of the pads of each test strip not reacting with the first plurality of different active chemicals.

DETAILED DESCRIPTION OF THE PREFERRED EMBODIMENTS

In the preferred embodiment of the present invention, an improved test screens medical dipsticks for contamination and accuracy. At least two inherently stable test solutions are used to accurately test each pad on a medical dipstick for both positive and negative results.

Figure 1A:
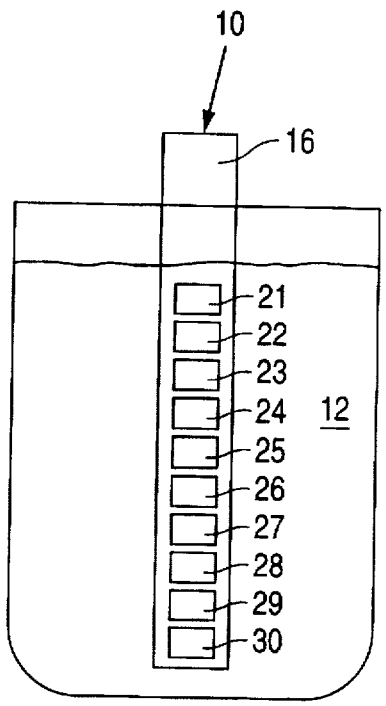
FIGS. 1a and 1b are views of two medical dipsticks being exposed to two test solutions.
Figure 1B:
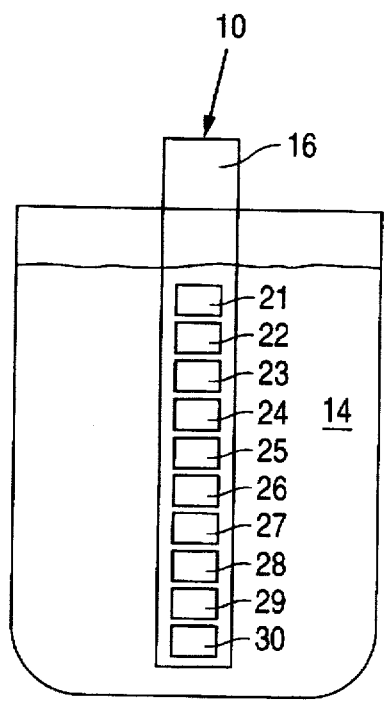

In the preferred embodiment, the invention involves medical dipsticks (10) as illustrated in FIG. 1. Each dipstick (10) includes an elongated strip of paper or plastic (16), and a plurality of pads (21-30, in this case 10 pads). Each pad (21-30) contains a different reactive chemical or reagent that visually reacts to different substances, such as different analytes. Therefore, if the dipstick (10) is dipped into a fluid sample containing one or more of these substances, a visual reaction will occur on one or more pads (21-30). By knowing which pads test for what substance, the combination of color changes and the locations of those color changes from a single exposure of the sample to a medical dipstick (10) would visually indicate the status and/or composition of that sample. To test whether a particular container of dipsticks (10) is still usable and not inactivated, at least two test solutions (12) and (14) are prepared to test the dipsticks (10) for accuracy. In the preferred embodiment, two test solutions (12 and 14) are prepared. The two test solutions (12 and 14) together contain all of the substances being tested for. However, each test solution (12 or 14) only contains some of the substances being tested for, not all of them. Therefore, dipping a dipstick (10) into the first test solution (12) will result in only some of the pads (e.g. 21, 23, 25, 27, and 29) reacting to the first test solution (12). Dipping the dipstick (10) into the second test solution (14) results in a reaction only in those pads (e.g. 22, 24, 26, 28, and 30) that did not react to the first test solution (12). Therefore, by placing a first dipstick (10) into solution (12), and an identical dipstick (10) into solution (14), each pad type (21-30) is tested once for a positive reaction and once for a negative reaction. By knowing which solution each pad (21-30) should react to, it can be determined whether the dipsticks (10) are still active and usable. Further, the different combinations of chemicals in solutions (12) and (14) can be selected so that each test solution (12 and 14) is stable.

Examples of test solutions (12) and (14), with test strip (10) are: Example I: A buffered saline solution containing hemoglobin, protein, bilirubin and glucose. Example II: A buffered saline solution containing analogs of urobilinogen and leukocyte esterase, a ketone, and sodium nitrite.

The method of the present invention and the control solutions are contrasted with the control solutions of the prior art. As previously discussed, in the prior art two control solutions are prepared. A first control solution would cause all of the pads (21–30) of the dipstick to change its visual indicator, e.g. its color, upon detection of certain fluid analytes, reacting to the reagent(s) mounted on that particular pad. A second control solution would cause none of the pads (21–30) to change its visual indicator. For example, one of the pads, e.g. (21), of dipstick (10) measures bilirubin activity. Thus, a first control solution would contain bilirubin which is detected by pad (21), and causes a change in the color thereof. Suppose, however, the dipstick also has a pad, e.g. (22), which tests for nitrite. Upon detecting the presence of nitrite, pad (22) would change its visual indicator. If nitrite were present in the first control solution, together with bilirubin also in the first control solution (to test pad (21), the nitrite and/or bilirubin would be degraded. Hence the shelf life of the first control solution would be limited.

In contrast with the method and control solutions of the prior art, this problem is overcome in the present invention. For example, bilirubin can be part of a mixture of analytes in a first control solution that tests for reaction of pads (21, 23, 25, 27, and 29). Nitrite can be in the second control solution that tests for pads (22, 24, 26, 28, and 30). In this manner, nitrite is not placed in the same control solution as bilirubin, thereby eliminating interaction between these analytes when they are included in the same control solution.

Finally, in the prior art, because of the problem of interaction between analytes in the same control solution, some control solutions did not provide for the testing of all reagents on all pads by the control solution. Instead, in the "active" control solution in which a positive test was developed for all reagents, some of the pads were merely stained to effect a change in a visual indicator.

In contrast, with the method of the present invention and the control solutions developed, the analytes in the control solutions, collectively, can test for the actual activity of all the reagents on all of the pads on the dipstick.

Although the preferred embodiment has been described in which the control solutions consist of two mixtures of analytes, the invention need not be so limited. In addition, although a preferred embodiment has been described in which the control solutions are useful for testing medical dipsticks, other applications of the method of the present invention and uses of the control solutions of the present invention are also contemplated. In particular, for example, the present invention can be used to test multiple chemicals each of which is not "bound" or "affixed" to a pad. The chemicals can be in solution. The analytes in one control solution can react with some of the multiple chemicals in the solution to be tested causing emission or absorption of light at characteristic wavelengths, which can be detected by, for example, a spectrophotometer. A second control solution can react with other chemicals in the solution causing emission or absorption of light which can be detected. Each of the first and second control solutions contain chemicals which do not react with one another.

What is claimed is:

1. A plurality of control solutions for testing a mixture of a plurality of different reactive chemicals, the plurality of control solutions comprising:

a first control solution containing a mixture of a first plurality of different active chemicals, each of said first plurality of different active chemicals for reacting chemically with a different one of said reactive chemicals to generate a first visual indicator, said first plurality of different active chemicals not reacting chemically with all of the different reactive chemicals; and one or more second control solutions containing a mixture of a second plurality of different active chemicals, each of said second plurality of different active chemicals for reacting chemically with a different one of said reactive chemicals to generate a second visual indicator different than said first visual indicator, said second plurality of different active chemicals not reacting chemically with any of the different reactive chemicals reacting with said first plurality of different active chemicals; collectively said second plurality of different active chemicals for reacting chemically with all of the different reactive chemicals not reacting to said first plurality of different active chemicals.

2. The plurality of control solutions of claim 1 wherein said first plurality of different active chemicals are non-reactive with one another.

3. The plurality of control solutions of claim 2 wherein said second plurality of different active chemicals are non-reactive with one another.

4. The plurality of control solutions of claim 1 wherein said first and second pluralities of different active chemicals react chemically with reactive chemicals affixed to a strip, with each different reactive chemical being affixed in a pad, physically separated from one another.

5. An analyte control solution system for testing a plurality of identical testing mixtures, each testing mixture containing a plurality of different reactive chemicals, the analyte control solution system comprising:

a first mixture of a first plurality of different analytes, each of said first plurality of different analytes not reacting with one another, and each reacting with a different one of the plurality of different reactive chemicals to generate a first visual indicator, said first plurality of different analytes not reacting with all of the different reactive chemicals of each testing mixture; and a second mixture of a second plurality of different analytes, said second mixture physically separated from said first mixture, each of said second plurality of different analytes not reacting with one another, and each reacting with a different one of said plurality of different reactive chemicals to generate a second visual indicator different than said first visual indicator, said second plurality of different analytes not reacting with any of the plurality of different reactive chemicals reacting to the analytes of said first mixture; collectively said second plurality of different analytes for reacting with all of the different reactive chemicals in each testing mixture not reacting to said first plurality of different analytes.

6. The analyte control solution system of claim 5, wherein each of said plurality of different reactive chemicals is affixed to a test strip.

7. A method of testing the integrity of a plurality of identical test strips, wherein each test strip has a plurality of different reactive chemicals attached thereto, said method comprising:

reacting a first test strip with a first control solution to produce a first visual indicator associated with each of one or more, but not all, of said plurality of different reactive chemicals; said first control solution containing a mixture of a first plurality of different analytes, not reacting with one another;

reacting a second test strip with a second control solution different from said first control solution to produce a second visual indicator different from said first visual indicator and associated with each of one or more, but not all, of said plurality of different reactive chemicals, different from the different reactive chemicals reacting in said first test strip; said second control solution containing a mixture of a second plurality of different analytes that are different from said first plurality of different analytes and do not react with one another;

wherein the first and second visual indicators produced from the reactive chemicals reacting with said first and second control solutions determine the integrity of other identical test strips.

* * * * *